United States Patent
Honda et al.

(10) Patent No.: US 9,039,176 B2
(45) Date of Patent: May 26, 2015

(54) CORNEAL ENDOTHELIAL CELL PHOTOGRAPHING APPARATUS

(75) Inventors: Naoto Honda, Okazaki (JP); Michihiro Takii, Aichi (JP)

(73) Assignee: NIDEK CO., LTD., Aichi (JP)

( * ) Notice: Subject to any disclaimer, the term of this patent is extended or adjusted under 35 U.S.C. 154(b) by 64 days.

(21) Appl. No.: 13/435,864

(22) Filed: Mar. 30, 2012

(65) Prior Publication Data
US 2012/0249958 A1 Oct. 4, 2012

(30) Foreign Application Priority Data

Mar. 31, 2011 (JP) .................. 2011-081047
Mar. 31, 2011 (JP) .................. 2011-081048

(51) Int. Cl.
  *A61B 3/15* (2006.01)
  *A61B 3/14* (2006.01)
  *A61B 3/10* (2006.01)

(52) U.S. Cl.
  CPC ............... *A61B 3/152* (2013.01); *A61B 3/145* (2013.01); *A61B 3/1005* (2013.01)

(58) Field of Classification Search
  CPC ....... A61B 3/1005; A61B 3/152; A61B 3/145
  USPC .................................................. 351/208, 206
  See application file for complete search history.

(56) References Cited

U.S. PATENT DOCUMENTS

| | | | | |
|---|---|---|---|---|
| 5,381,194 A | * | 1/1995 | Nishio et al. | 351/208 |
| 5,436,679 A | * | 7/1995 | Ohtsuka et al. | 351/206 |
| 5,548,354 A | * | 8/1996 | Kasahara et al. | 351/206 |
| 5,694,197 A | * | 12/1997 | Tsukada et al. | 351/206 |
| 5,757,462 A | * | 5/1998 | Nanjo | 351/206 |
| 6,164,778 A | * | 12/2000 | Takagi et al. | 351/206 |
| 7,695,139 B2 | * | 4/2010 | Ishikura | 351/208 |
| 2005/0068496 A1 | * | 3/2005 | Ichikawa | 351/206 |
| 2006/0268230 A1 | * | 11/2006 | Kogawa et al. | 351/206 |
| 2007/0146636 A1 | * | 6/2007 | Ishikura | 351/221 |
| 2008/0055544 A1 | * | 3/2008 | Nishio et al. | 351/208 |
| 2008/0212029 A1 | * | 9/2008 | Ichikawa | 351/208 |

FOREIGN PATENT DOCUMENTS

| | | |
|---|---|---|
| JP | A-6-46999 | 2/1994 |
| JP | A-6-189909 | 7/1994 |
| JP | A-7-79924 | 3/1995 |
| JP | A-8-206080 | 8/1996 |
| JP | A-09-098951 | 4/1997 |

* cited by examiner

*Primary Examiner* — Thomas K Pham
*Assistant Examiner* — Marin Pichler
(74) *Attorney, Agent, or Firm* — Oliff PLC

(57) ABSTRACT

A corneal endothelial cell photographing apparatus comprises: a main unit including: an illumination optical system for illuminating illumination light from an illumination light source toward a cornea of an examinee's eye from an oblique direction; an imaging optical system for obtaining a corneal endothelial cell image by receiving, through an imaging element, reflection light from the cornea including corneal endothelial cells; and a fixation optical system including a plurality of fixation targets and for guiding a fixation direction of the examinee's eye; a drive unit to relatively move the main unit with respect to the examinee's eye; a serial photographing unit to obtain endothelial images in series at different photographing positions in previously set up-and-down and right-and-left directions; and a monitor to display the obtained endothelial image.

15 Claims, 11 Drawing Sheets

CORNEAL ENDOTHELIAL CELL PHOTOGRAPHING APPARATUS

CROSS-REFERENCE TO RELATED APPLICATIONS

This application is based upon and claims the benefit of priority from the prior Japanese Patent Applications NO. 2011-081047, filed Mar. 31, 2011 and NO. 2011-081048, filed Mar. 31, 2011, the entire contents of which are incorporated herein by reference.

BACKGROUND

1. Technical Field

The present invention relates to a corneal endothelial cell photographing apparatus for photographing a cell image of the corneal endothelium of an examinee's eye.

2. Related Art

Conventionally, there is known an apparatus arranged to obtain a cell image of corneal endothelium in a noncontact manner by irradiating illumination light from an illumination light source to a cornea from an oblique direction and receives reflection light from the cornea by an imaging element (see Patent Document 1).

Meanwhile, as the above apparatus, there are known for example an apparatus provided with a focus detection sensor for detecting a focused state with respect to corneal endothelium and arranged to perform photographing after moving a main unit to an in-focus position with respect to the corneal endothelium (see Patent Document 1) and an apparatus arranged to perform serial photographing while moving a main unit in a predetermined direction (see Patent Document 2).

In the case of the conventional apparatuses, however, it takes long to obtain many endothelial images, resulting in a burden on an examiner and an examinee. For instance, to obtain endothelial images of many sites by changing fixation positions, an examinee needs to change his/her visual line every time the fixation position is changed, and such a photographing operation is repeated.

As represented by photographing to many sites, lengthening of an examination time causes fatigue of eyes. Such eye fatigue increases involuntary eye movement. This results in deterioration of photographed images.

RELATED ART DOCUMENTS

Patent Documents

Patent Document 1: JP 8(1996)-206080 A
Patent Document 2: JP 7(1995)-079924 A

SUMMARY

The present invention has a purpose to provide a corneal endothelial cell photographing apparatus capable of smoothly obtaining endothelial images at different positions.

To achieve the above purpose, one aspect of the invention provides a corneal endothelial cell photographing apparatus comprising: a main unit including: an illumination optical system for illuminating illumination light from an illumination light source toward a cornea of an examinee's eye from an oblique direction; an imaging optical system for obtaining a corneal endothelial cell image by receiving, through an imaging element, reflection light from the cornea including corneal endothelial cells; and a fixation optical system including a plurality of fixation targets and for guiding a fixation direction of the examinee's eye; a drive unit to relatively move the main unit with respect to the examinee's eye; a serial photographing unit to obtain endothelial images in series at different photographing positions in previously set up-and-down and right-and-left directions; and a monitor to display the obtained endothelial image.

DETAILED DESCRIPTION

Figure 1:
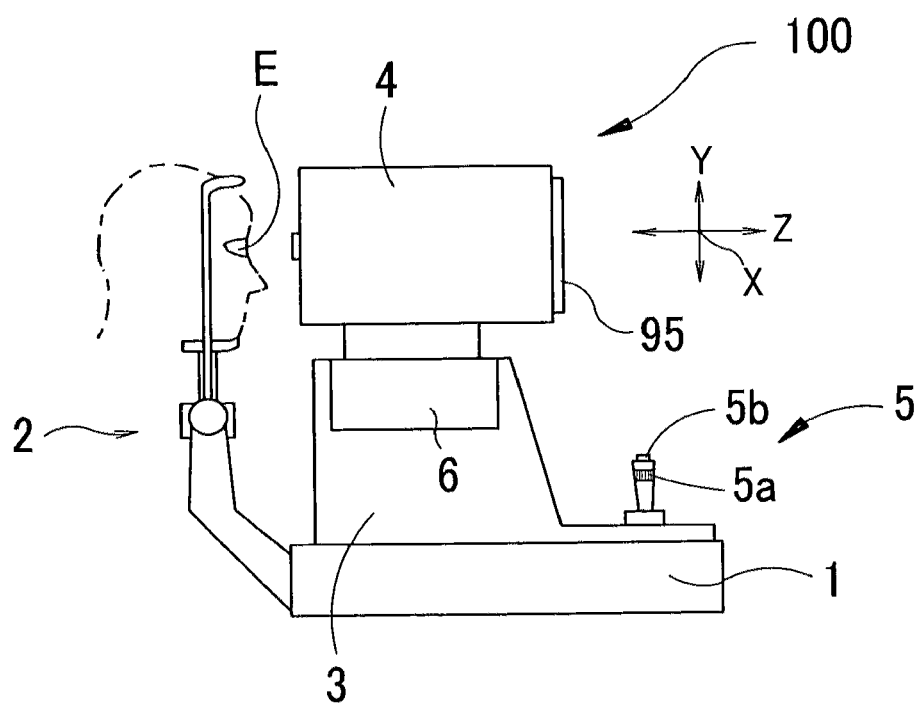
FIG. 1 is an external side view showing a configuration of a corneal endothelial cell photographing apparatus in a preferred embodiment.

In the following detailed description, for purpose of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

A detailed description of a preferred embodiment of embodying the present invention will now be given referring to the accompanying drawings. FIG. 1 is an external side view showing a configuration of a corneal endothelial cell photographing apparatus in the present embodiment.

An apparatus 100, which is a so-called stationary apparatus, includes a base 1, a head support unit 2 attached to the base 1, a movable table 3 provided to be movable on the base 1 by a sliding mechanism not shown, and a photographing part (a main unit) 4 provided to be movable relative to the movable table 3 and to contain a photographing system and optical systems mentioned later.

The photographing part 4 is moved, by a XYZ drive part 6 provided in the movable table 3, in a right-and-left direction (X direction), up-and-down direction (Y direction), and back-and-forth direction (Z direction) with respect to an examinee's eye E. The movable table 3 is moved in the X and Z directions on the base 1 by operation of a joystick 5. Further, when an examiner rotates a rotation knob 5a, the photographing part 4 is moved in the Y direction by Y-drive of the XYZ drive part 6. At a top of the joystick 5, a start switch 5b is provided. A display monitor 95 is placed on an examiner side of the photographing part 4. In the present embodiment, the photographing part 4 is moved relative to the eye E by a sliding mechanism not shown or the XYZ drive part 6.

Instead of providing the mechanical sliding mechanism to move the photographing part 4, it may be configured to move the photographing part 4 with respect to right and left eyes by motor-driving the drive part 6. The present apparatus may also be configured to have a touch panel as a manual operating member such as the joystick 5.

Figure 2A:
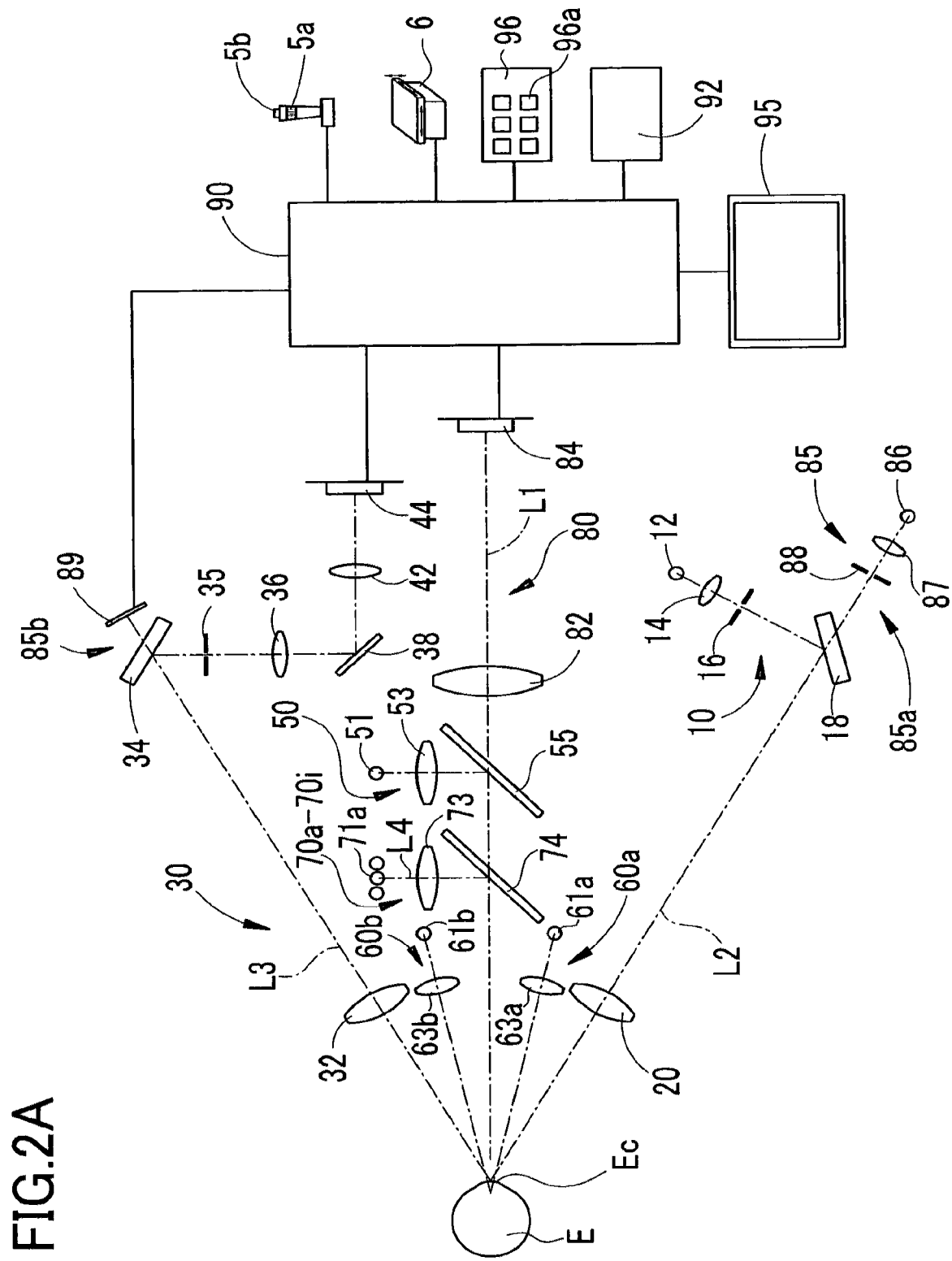
FIG. 2A is a schematic diagram showing one example of an optical arrangement of optical systems contained in a photographing part when seen from above and a configuration of a control system.
Figure 3:
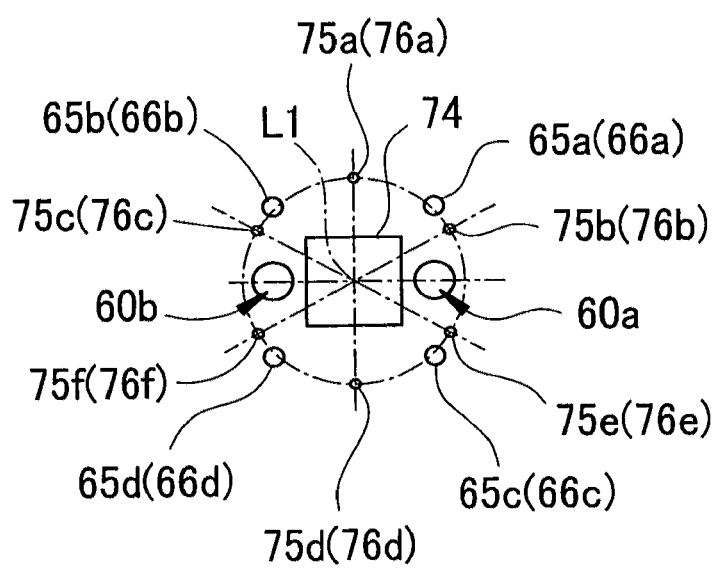
FIG. 3 is a diagram showing a first projecting optical system and a second projecting optical system when seen from an examinee's side.

FIG. 2A is a schematic configuration diagram showing one example of the optical arrangement of the optical systems contained in the photographing part 4 when seen from above and the configuration of a control system. FIG. 3 is a diagram of a first projecting optical system and a second projecting optical system seen from an examinee side. The whole configuration of the optical systems includes an illumination optical system 10, an imaging optical system 30, a front projecting optical system 50, first projecting optical systems 60a and 60b, second projecting optical systems 65a to 65d (see FIG. 3), internal fixation optical systems 70a to 70i, external fixation optical systems 75a to 75f (see FIG. 3), an anterior segment observation optical system 80, and a Z alignment detecting optical system 85.

The illumination optical system 10 irradiates illumination light from an illumination light source 12 toward a cornea Ec from an oblique direction. The illumination optical system 10 includes the illumination light source 12 (e.g., a visible LED, a flash lamp) that emits visible light to be used for endothelium photographing, a condensing lens 14, a slit plate 16, a dichroic mirror 18 that reflects visible light but transmits infrared light, and a light projection lens 20. Light emitted from the illumination light source 12 illuminates the slit plate 16 through the condensing lens 14. The slit light having passed through the slit plate 16 is converged by the light projection lens 20 via the dichroic mirror 18 and then irradiated onto a cornea. Herein, the slit plate 16 is arranged in a position conjugate with the cornea Ec with respect to the projection lens 20.

The imaging optical system 30 causes an imaging element to receive reflection light from the cornea Ec including endothelial cells and thereby obtains an endothelial cell image. The imaging optical system 30 is symmetric to the illumination optical system 10 with respect to an optical axis L1 and includes an objective lens 32, a dichroic mirror 34 that reflects visible light but transmits infrared light, a mask (slit) 35, a first image-forming lens 36, a total reflection mirror 38, a second image-forming lens 42, and a first two-dimensional imaging element (e.g., a two-dimensional CCD (charge coupled device) image sensor, a two dimensional CMOS (complementary metal oxide semiconductor) image sensor, etc.) 44 specifically designed to obtain cell images. The mask 35 is arranged in a substantially conjugate position with the cornea Ec with respect to the objective lens 32. The first image-forming lens 36 and the second image-forming lens 42 form an image-forming optical system to form an endothelial image on the imaging element 44. This imaging element 44 is placed in a substantially conjugate position with the cornea Ec with respect to a lens system of the imaging optical system 30.

Corneal reflection light generated by the illumination optical system 10 travels along an optical axis L3 (an oblique direction) and is converged by the objective lens 32, then reflected by the dichroic mirror 34 to converge on the mask 35 once, whereby shielding the light that will become noise when an endothelial cell image is to be obtained. Light having passed through the mask 35 forms an image on the imaging element 44 via the first image-forming lens 36, the total reflection mirror 38, and the second image-forming lens 42. Accordingly, a corneal endothelial cell image at a high magnification is obtained. An output of the imaging element 44 is connected to a controller 90 and the obtained cell image is stored in a memory 92. Further, the cell image is displayed on a monitor 95.

The front projecting optical system 50 is arranged to project an alignment index toward the cornea Ec from front. This optical system 50 includes an infrared light source 51, a light projection lens 53, and a half mirror 55, to project infrared light for XY alignment detection to the cornea Ec from a direction along the observation optical axis L1. Infrared light emitted from the light source 51 is converted into parallel light by the light projection lens 53 and reflected by the half mirror 55, projected onto the center portion of the cornea Ec, forming an index i10 (see FIG. 4B).

The first projecting optical systems 60a and 60b project infinite alignment indexes toward the cornea Ec from oblique directions. The first projecting optical systems 60a and 60b are arranged at respective predetermined angles to the optical axis L1. The first projecting optical systems 60a and 60b respectively include infrared light sources 61a and 61b and collimator lenses 63a and 63b, and are arranged symmetric with respect to the optical axis L1 to project infinite indexes to the eye E (see FIG. 2A). It is to be noted that the first projecting optical systems 60a and 60b are placed on substantially the same meridian line as the horizontal direction passing the optical axis L1 (see FIG. 3).

Figure 4A:
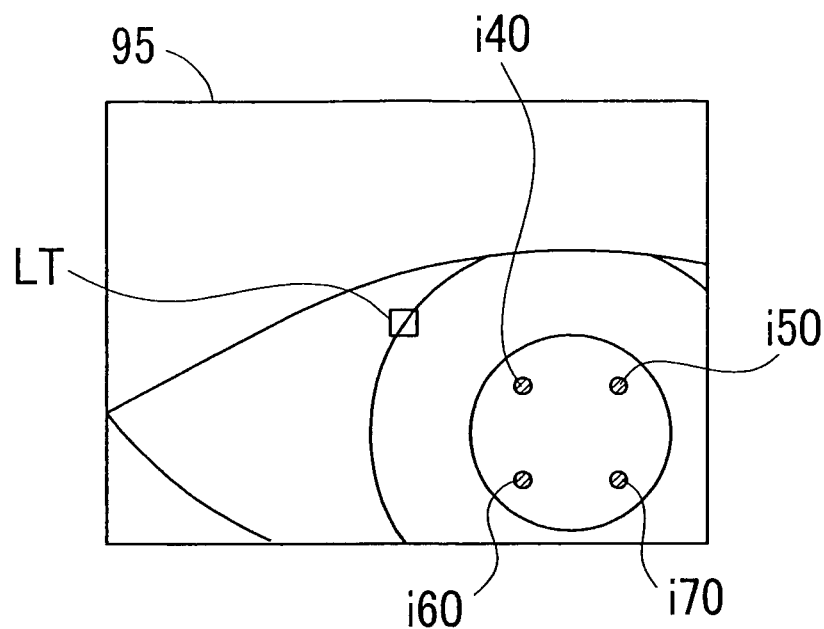
FIGS. 4A and 4B are diagrams showing one example of an anterior segment observation screen when endothelium of a central part of a cornea is to be photographed, FIG. 4A showing a display example in which alignment is displaced and FIG. 4B showing a display example in which alignment is proper.
Figure 4B:
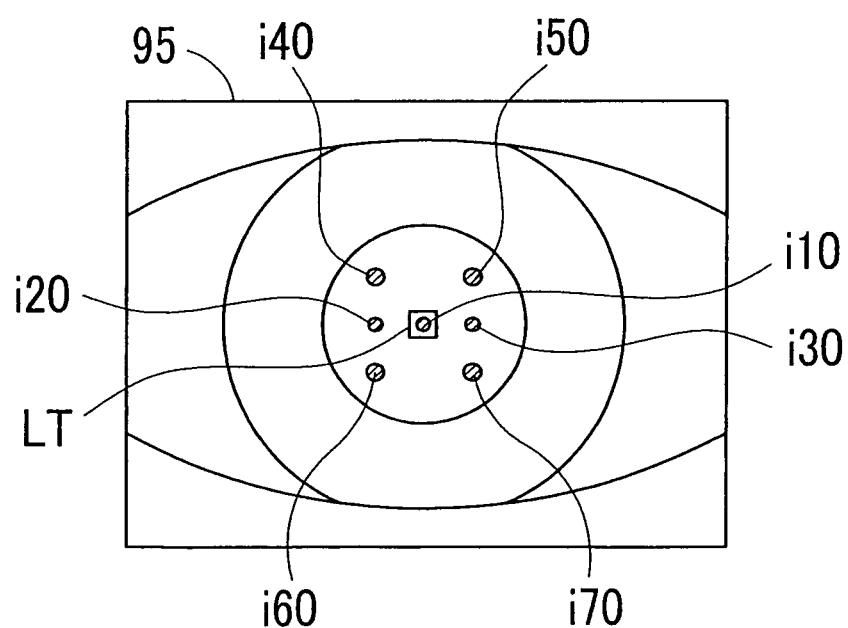

Lights emitted from the light sources 61a and 61b are collimated by the collimator lenses 63a and 63b respectively and then projected onto the cornea Ec, forming indexes i20 and i30 (see FIG. 4B).

The second projecting optical systems 65a to 65d project finite alignment indexes toward the cornea Ec respectively from a plurality of oblique directions. Those optical systems 65a to 65d are arranged obliquely with respect to the optical axis L1. The second projecting optical systems 65a to 65d respectively include infrared light sources 66a to 66d and are arranged symmetric with respect to the optical axis L1 to project finite indexes onto the eye E. It is to be noted that the second projecting optical systems 65a and 65b are placed above the optical axis L1 and at the same level as each other in the Y direction. The second projecting optical systems 65c and 65d are placed below the optical axis L1 and at the same level as each other in the Y direction. The second projecting optical systems 65a and 65b are arranged in a symmetric relation with the second projecting optical systems 65c and 65d with respect to the optical axis L1.

Herein, lights from the light sources 66a and 66b are irradiated toward an upper part of the cornea Ec from upper oblique directions to form indexes i40 and I50 which are virtual images of the light sources 66a and 66b. Lights from the light sources 66c and 66d are irradiated toward a lower part of the cornea Ec from lower oblique directions to form indexes i69 and i70 which are virtual images of the light sources 66c and 66d (see FIGS. 4A and 4B).

According to the index projecting optical system mentioned above, the index i10 is formed at a corneal vertex of the eye E (see FIG. 4B). The indexes i20 and i30 by the first projecting optical systems 60a and 60b are formed in the same horizontal positions as the index i10 and symmetric to each other with respect to the index i10. Furthermore, the indexes i40 and i50 by the second projecting optical systems 65a and 65b are formed above the index i10 and symmetric to each other with respect to the index i10. The indexes i60 and i70 by the second projecting optical systems 65c and 65d are formed below the index i10 and symmetric to each other with respect to the index i10.

The internal fixation optical systems 70a to 70i are arranged to project fixation targets onto the eye E from inside. Those optical systems 70a to 70i include visible light sources (fixation lamps) 71a to 71i (see FIG. 2B), a light projection lens 73, and a dichroic mirror 74 that reflects visible light but transmits infrared light. Visible light emitted from the light source 71 is converted into parallel light by the light projection lens 73, then is reflected by the dichroic mirror 74 and projected onto a fundus of the eye E. An external fixation optical system not shown is placed near the first projecting optical system and the second projecting optical system.

Figure 2B:
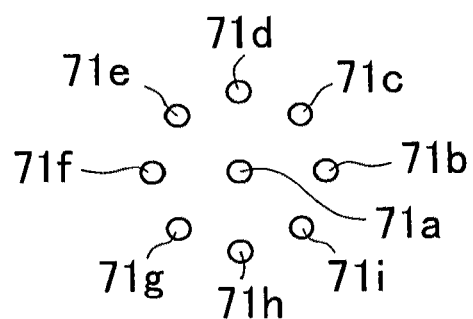
FIG. 2B is a diagram showing an internal fixation optical system shown in FIG. 2A.

The internal fixation optical systems 70a to 70i include a plurality of fixation targets arranged in different positions in a direction perpendicular to an optical axis L4 to guide the fixation direction of the eye E to each direction. The internal fixation optical systems 70a to 70i are provided inside the photographing part 4. For instance, the visible light source 71a is placed near the optical axis L4 and used to guide the eye E to a front direction to obtain an endothelial image of the center portion of the cornea. A plurality of visible light sources 71b to 71i are placed in one circle centered on the optical axis L4 and arranged at predetermined angular intervals when seen from an examinee side. In FIG. 2B, they are arranged at each 45° interval, i.e., at 0°, 45°, 90°, 135°, 180°, 225°, 270°, and 315°. The visible light sources 71b to 71i are used to guide the visual line of the eye E to peripheral directions to obtain endothelial images in peripheral points around the corneal center.

The external fixation optical systems 75a to 75f project fixation targets from outside. Those optical systems 75a to 75f have a plurality of fixation targets arranged in different positions in the X-Y direction to change the fixation direction of the examinee's eye at a larger angle than the internal fixation optical system 70. The external fixation optical systems 75a to 75f are provided on the outside of the photographing part 4 and close to the eye E. For example, the external fixation optical systems 75a to 75f have visible light sources (fixation lamps) 76a to 76f and are arranged in a circle centered on the optical axis L1 and at 2, 4, 6, 8, 10, and 12-o'clock positions when seen from the examinee. The visible light sources 76a to 76f are used to guide the visual line of the eye E to a peripheral direction to thereby obtain an endothelial image in the peripheral part of the cornea. In this case, an endothelial cell image more outside than the image obtained by the visible light sources 71b to 71i is acquired.

When a lower part of the cornea is to be photographed, for instance, the position of the fixation lamps (fixation targets) is set to an upper side to guide the fixation of the eye E in an upward direction. When an upper part of the cornea is to be photographed, the position of the fixation lamps (fixation targets) is set to a lower side to guide the fixation of the eye E in a downward direction.

Returning to FIG. 2A. The anterior segment observation optical system 80 is arranged to observe an anterior segment image from front. This optical system 80 includes an objective lens 82, a two-dimensional second imaging element 84, different from the first imaging element 44 for obtaining an anterior segment front image, to capture an anterior segment image and alignment indexes through the second imaging element 84. The two-dimensional imaging element 84 may include a two-dimensional CCD image sensor and a two-dimensional CMOS image sensor, for example.

The anterior segment illuminated by an anterior segment illumination light source not shown is captured by the two-dimensional imaging element 84 via the dichroic mirror 75, the half mirror 55, and the objective lens 82. Similarly, the corneal reflection image formed by the front projecting optical system 50, the first projecting optical systems 60a and 60b, and the second projecting optical systems 65a to 65d is received by the two-dimensional imaging element 84.

An output of the imaging element 84 is connected to the controller 90 and thus the monitor 95 displays the anterior segment image imaged by the imaging element 84 as shown in FIGS. 4A and 4B. A reticle LT electronically displayed on the monitor 95 represents a reference for XY alignment. The observation optical system 80 is also used as a detection optical system for detecting an alignment state of the photographing part 4 with respect to the eye E.

The Z alignment detecting optical system 85 is arranged to detect the alignment state of the photographing part 4 in the Z direction with respect to the eye E. This optical system 85 includes a light projecting optical system 85a to project detection light toward the cornea Ec from an oblique direction and a light receiving optical system 85b to receive corneal reflection light generated by the light projecting optical system 85a. The optical axis L2 of the light projecting optical system 85a and the optical axis L3 of the light receiving optical system 85b are placed in positions symmetric with respect to the observation optical axis L1.

The light projecting optical system 85a includes, for example, an illumination light source 86 that emits infrared light, a condensing lens 87, a pin-hole plate 88, and the lens 20. Herein, the pin-hole plate 88 is placed in a position substantially conjugate with the cornea Ec with respect to the lens 20. The light receiving optical system 85b includes, for example, the lens 32 and a one-dimensional light-receiving element (a line sensor) 89. Herein, the one-dimensional light-receiving element 89 is placed in a position substantially conjugate with the cornea Ec with respect to the lens 32.

Infrared light emitted from the light source 86 illuminates the pin-hole plate 88 through the condensing lens 87. Light having passed through a pin hole of the pin-hole plate 88 is projected onto the cornea Ec through the lens 20. Corneal reflection light is then received by the light-receiving element 89 via the lens 32 and the dichroic mirror 34.

An output of the light-receiving element 89 is connected to the controller 90 and used for Z alignment with respect to the eye E. Herein, the alignment light received on the light-receiving element 89 changes its light receiving position depending on a positional relationship between the photographing part 4 and the eye E in the Z direction. For instance, the controller 90 detects the position of corneal reflection light based on a detection signal from the light-receiving element 89 and detects the alignment state in the Z direction. The alignment detection using the light-receiving element 89 is utilized for accurate alignment to the eye E.

The controller 90 controls the whole apparatus. To the controller 90, there are connected the rotation knob 5a, the start switch 5b, the XYZ drive part 6, the two-dimensional imaging elements 44 and 84, each light source, the memory 92 serving as a storage means, the monitor 95, and the operating part 96.

For instance, the controller 90 controls display of the monitor 95. Furthermore, the controller 90 detects the alignment state of the photographing part 4 in the X-Y-Z direction with respect to the eye E based on a light reception result of the alignment indexes. The controller 90 outputs a command signal to move the photographing part 4 based on the detection result. The controller 90 further detects the alignment state of the photographing part 4 in the Z direction with respect to the eye E based on the light reception result from the light-receiving element 89.

Operations of the apparatus having the above configuration will be explained below. FIGS. 4A and 4B show one example of the anterior segment observation screen when the endothelium of the corneal central part is to be photographed. Specifically, FIG. 4A shows a display example in which alignment is displaced and FIG. 4B shows a display example in which alignment is proper.

In this case, the light source 71a is turned on to guide the fixation direction of the eye E to the front. The examiner first asks the examinee to look at the fixation target. While observing the anterior segment image displayed on the monitor 95, the examiner makes alignment of the photographing part 4 with respect to the eye E.

After rough alignment is completed as above, a corneal index image formed by diffused light is detected on a light receiving plane of the imaging element 64 as shown in FIG. 4A. The controller 90 searches for a luminescent spot on the image from upper-left to lower-right coordinate positions on the screen. When the indexes i40, i50, i60, and i70 are detected, the controller 90 detects the position of the detected luminescent spot.

The controller 90 then detects, as a substantial corneal vertex, the center point of a rectangle defined by the indexes i40, i50, i60, and i70 and detects a misalignment direction and a deviation amount in the X-Y direction. The controller 90 controls driving of the drive part 6 to move the photographing part 4 in the X-Y direction so that the misalignment falls in a predetermined alignment tolerance range. Accordingly, automatic alignment in a wide range is enabled.

When the photographing part 4 is moved as above and thus the index i10 is detected, the controller 90 stops the alignment using the aforementioned indexes i40 to i70 and performs alignment using the index i10. The controller 90 discriminates between the index i10 and the indexes i40- to i70 from their positional relationship.

The controller 90 detects the coordinate position of the index i10 as a substantial corneal vertex and detects the misalignment direction and the deviation amount in the X-Y direction. The controller 90 controls driving of the drive part 6 to move the photographing part 4 in the X-Y direction so that the misalignment falls in a predetermined alignment tolerance range.

When the index i10 is detected as above, the infinite indexes i20 and i30 are similarly detected. By comparing the interval between the infinite indexes i20 and i30 detected as above and the interval between the finite indexes i60 and i70, the controller 90 determines the misalignment direction and the deviation amount in the Z direction (First alignment detection). The controller 90 then moves the photographing part 4 in the Z direction so that the misalignment in the Z direction falls in a predetermined tolerance range (First automatic alignment).

In this case, by utilizing the characteristics that the interval between the infinite indexes i20 and i30 changes little when the photographing part 4 is displaced in a working distance direction, whereas the interval between the finite indexes i60 and i70 changes, the controller 90 determines the alignment in the Z direction (for the details, see JP 6 (1994)-46999 A). As an alternative, the indexes i40 and i50 may be utilized instead of the indexes i60 and i70. As another alternative, the Z alignment may be detected based on a distance of the index (index height) from the optical axis L1.

When the alignment state is determined to be proper in the first Z alignment detection, the controller 90 stops operations for the first automatic alignment and then activates Second alignment detection in the Z direction using the detecting optical system 85 and Second automatic alignment based on a detection result thereof.

The controller 90 turns on the light source 86 to project alignment light onto the cornea Ec (the light source 86 may be turned on in advance) and also detects the corneal reflection light by the light-receiving element 89. The controller 90 controls driving of the drive part 6 based on a light reception result from the light-receiving element 89 and moves the photographing part 4 in the Z direction.

Figure 5:
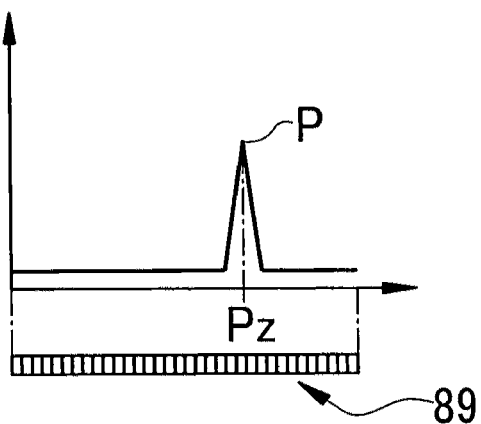
FIG. 5 is a graph showing an endothelial peak detected on a line sensor.

For instance, the controller 90 detects a peak P corresponding to the reflection light from corneal epithelium based on a light reception signal outputted from the light-receiving element 89, and then detects a position Pz of the epithelial peak on the light-receiving element 89 (see FIG. 5). The controller 90 drives the drive part 6 so that a peak of the light reception signal by the reflection light from the epithelium comes to a predetermined position (e.g., a center position) on the light-receiving element 89.

When the alignment state in the X-Y-Z direction meets the alignment completion condition by the above alignment operation, the controller 90 determines that the alignment in the X-Y-Z direction is completed properly and then generates a trigger signal.

<Reciprocating Photographing>

The following explanation is given to the case where the photographing part 4 is reciprocally moved, or shuttled, after completion of alignment and the endothelial images are photographed serially in both of a forward direction and a backward direction.

Figure 6:
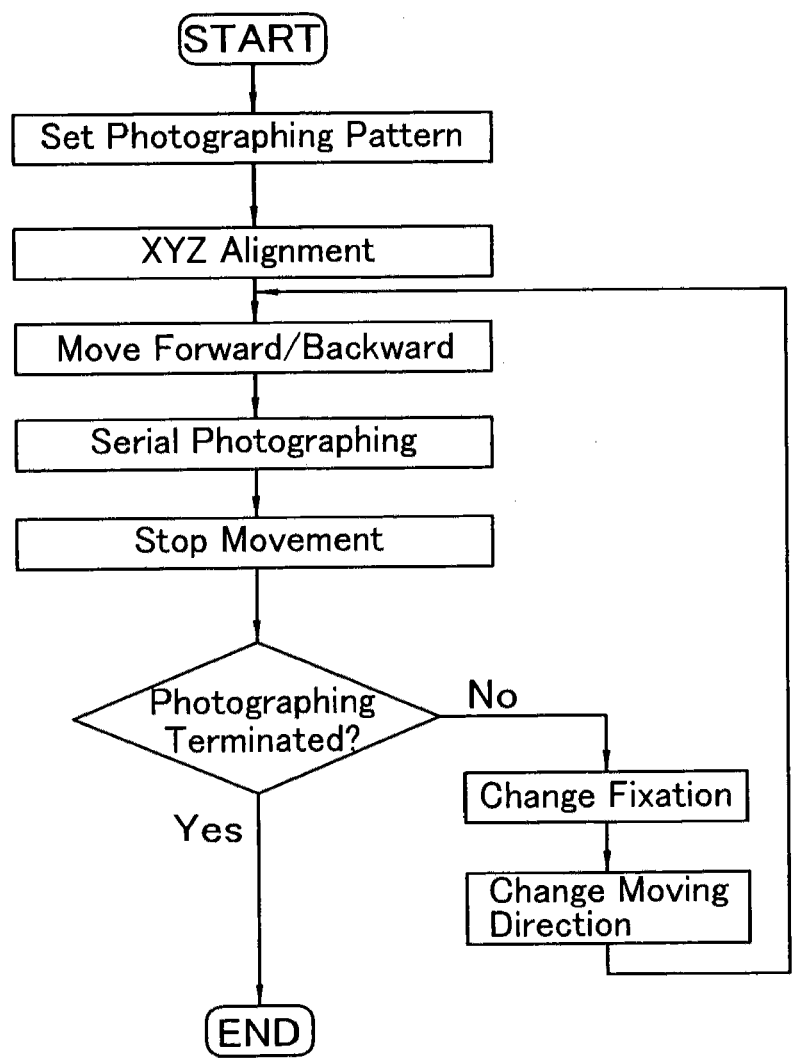
FIG. 6 is a flowchart showing one example of operations of the apparatus during reciprocating movement.

FIG. 6 is a flowchart showing one example of operations of the apparatus in reciprocating movement. The controller 90 generally controls driving of the drive part 6 to shuttle the photographing part 4 in predetermined directions. The controller 90 causes the illumination light source 12 to continuously emit light to obtain a plurality of endothelial images while moving the photographing part 4 in the forward direction. On the other hand, the controller 90 causes the illumination light source 12 to continuously emit light to obtain a plurality of endothelial images by the imaging element 44 while moving the photographing part 4 in the backward direction.

In the reciprocating photographing, the controller 90 may control the fixation optical system (e.g., the internal fixation optical systems 70a to 70i) to change presenting positions of the fixation targets according to the change of the moving direction of the photographing part 4.

<Setting of Photographing Pattern>

Figure 7A:
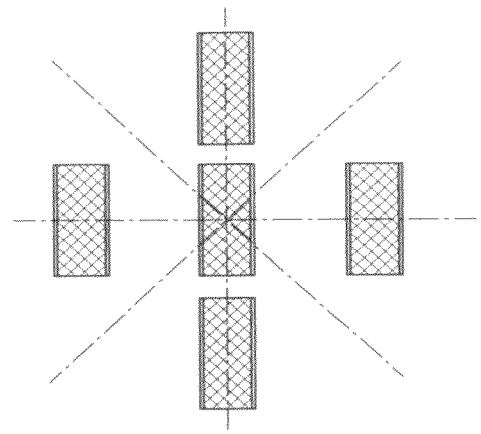
FIGS. 7A and 7B are diagrams showing one examples of photographing patterns.
Figure 7B:
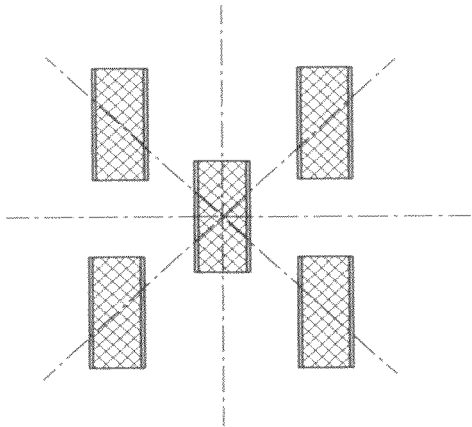

A photographing pattern in the endothelium photographing is first set. FIG. 7A shows a first photographing pattern in which photographing positions are set to an upper part, a lower part, a left part, and a right part of the cornea in addition to the corneal central part. FIG. 7B shows a second photographing pattern in which photographing positions are set to a right upper part, a right lower part, a left lower part, and a left upper part of the cornea.

The first photographing pattern (a cross-shaped pattern) is provided to photograph, as one group, an endothelial image of the central part of the cornea and the endothelial images of corneal parts in the upper, lower, right, and left positions with respect to the corneal central part. The second photographing pattern (an X-shaped pattern) is provided to photograph, as one group, the endothelial image of the corneal central part and the endothelial images of corneal parts in the oblique directions (at each 90° interval) with respect to the central part of the cornea. Herein, the second pattern is effective to check an endothelial state in each direction with respect to the corneal central part in a balanced manner.

In the case of the first photographing pattern, the light source 71a provided at the center and the light sources 71b, 71d, 71f, and 71h arranged in upper, lower, left, and right positions with respect to the light source 71a are used and turned on in sequence. In the case of the second photographing pattern, the light source 71a and the light sources 71c, 71e, 71g, and 71i arranged in oblique directions (at each 90° interval) with respect to the light source 71a are used and turned on in sequence.

In this case, the light source 71a is first turned on to photograph the endothelial image of the central part, and then the light sources (the light sources 71b to 71i) are turned on in sequence to photograph the endothelial images of the peripheral parts. In this case, it is preferable to sequentially turn on the adjacent fixation positions (for example, clockwise or counterclockwise).

The examiner selects a photographing pattern of the fixation target group to be presented to the examinee by use of a photographing pattern selection switch 96a provided in the operating part 96 of the apparatus. Based on the selected fixation target group, the controller 90 changes the presenting position of the fixation targets. In this case, an index indicating the photographing pattern may be displayed on the monitor 95 so that the examiner identifies the photographing pattern. This index may be a fixation target pattern.

The following explanation is given to the case where the first photographing pattern is set as the photographing pattern. For instance, the controller 90 first turns on the light source 71a to guide the eye E to look at the front direction. After the alignment state in the X-Y-Z direction meets the alignment completion condition by the aforementioned alignment operation, the controller 90 determines that the alignment in the X-Y-Z direction is properly completed and then generates a trigger signal.

Upon generation of the trigger signal, the controller 90 causes the light source 12 to continuously turn on and also controls driving of the drive part 6 to move the photographing part 4 forward toward the eye E. The controller 90 detects, through the two-dimensional imaging element 44, the reflection light from the cornea obtained by the visible illumination light from the light source 12. At that time, preferably, the controller 90 causes the light source 12 to emit light with such a light intensity at which the epithelium reflection light is detected but the endothelium reflection light is not detected. While moving the photographing part 4 in the Z direction, preferably, the controller 90 continues to operate the automatic alignment in the X-Y direction.

<Detection of Brightness of Output Image>

Figure 8:
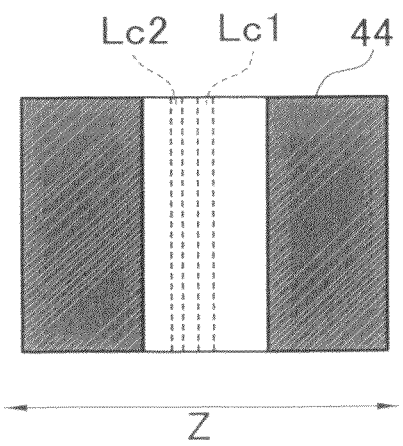
FIG. 8 is a diagram showing one example when a light receiving state of a corneal image is to be determined based on an output image from an imaging element.

The controller 90 detects an output image from the imaging element 44 and controls the light source 12 and the drive part 6 based on a detection result. FIG. 8 is a diagram showing one example to determine a light reception state of a corneal image based on the output image from the imaging element 44. In FIG. 8, a white rectangular center region corresponds to the aperture of the mask placed before the imaging element 44 and right and left black hatched regions correspond to a light shielding portion of the mask 35.

For example, to detect the light reception state of the corneal image, the controller 90 sets a first detection region Lc1 and a second detection region Lc2, each extending in an intersecting direction to a thickness direction (Z direction in FIG. 8) of the cornea. The first detection region Lc1 is set to detect a light reception state of the epithelium reflection light and the second detection region Lc2 is set to detect a light reception state of the endothelium reflection light. The controller 90 calculates a total value SLC1 of luminance values of all pixels in the first detection region Lc1. The controller 90 also calculates a total value SLC2 of luminance values of all pixels in the second detection region Lc2.

Figure 9A:
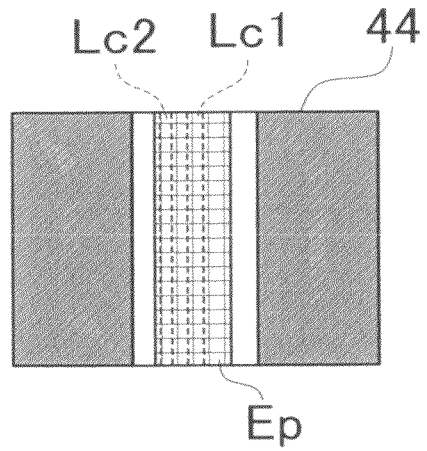
FIGS. 9A to 9C are diagrams showing changes of a light receiving state of corneal reflection light when the photographing part is moved forward.
Figure 9B:
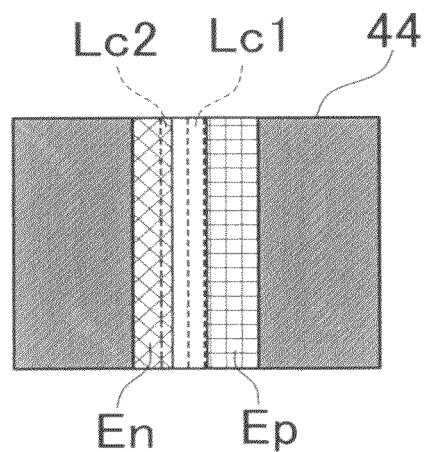
Figure 9C:
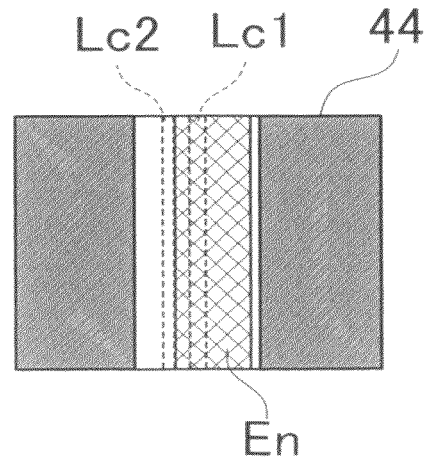
Figure 10A:
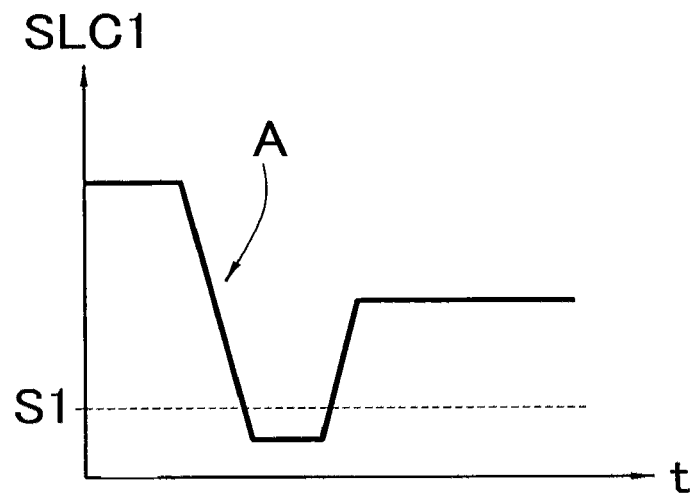
FIGS. 10A and 10B are graphs showing changes in each total value in time sequence when the photographing part is moved forward.
Figure 10B:
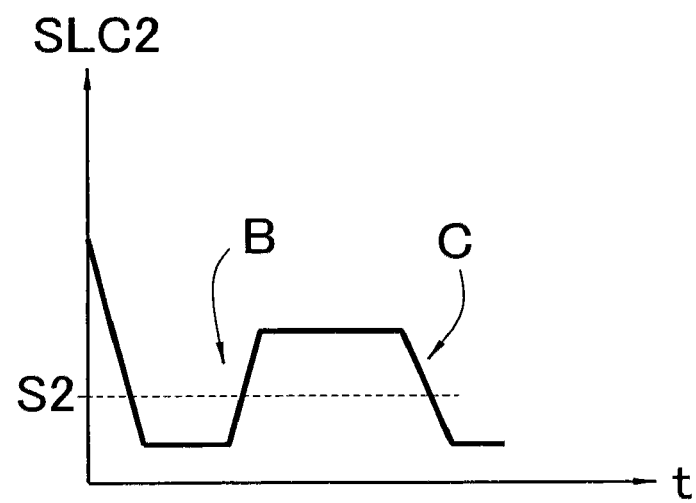

FIGS. 9A to 9C are diagrams showing changes of a light receiving state of the corneal reflection light when the photographing part 4 is moved forward. FIGS. 10A and 10B are graphs showing changes in the total values SLC1 and SLC2 in time sequence when the photographing part 4 is moved forward. FIG. 10A corresponds to the total value SLC1 and FIG. 10B corresponds to the total value SLC2.

FIG. 9A is a diagram showing the state appearing when alignment in the X-Y-Z direction is completed. At that time, the epithelium reflection light Ep is received on the first region Lc1. Accordingly, the first total value SLC1 is calculated as a high value corresponding to the epithelium reflection (see FIG. 10A).

When the photographing part 4 is moved forward, the epithelium reflection light Ep is moved rightward on a drawing sheet of FIGS. 9A to 9C. When the epithelium reflection light Ep passes the detection region Lc1, the total value SLC1 greatly decreases (see an inclination A in FIGS. 9B and 10A). When the total value SLC1 decreases below a predetermined threshold value S1, the controller 90 increases the light intensity of the light source 12 to such a level as that the endothelial image appears on the image outputted from the imaging element 44. Thus, the endothelium reflection light En is enabled to be detected by the imaging element 44.

After increasing the light intensity of the light source 12, the controller 90 continues to move the photographing part 4 forward and causes the memory 92 to store, at any time, images outputted serially from the imaging element 44. The two-dimensional imaging element 44 serially outputs imaging signals according to the frame rate to the controller 90. Accordingly, a plurality of imaged images of the endothelium are obtained. The controller 90 causes the memory 92 to store, as a still image, an image satisfying a certain condition (e.g., an endothelial cell image is property obtained) from the outputted images. Thus, the endothelial cell image is photographed. In this case, the controller 90 may store a previously set predetermined number of images in the memory 92. The controller 90 then causes the monitor 95 to display the photographed image stored in the memory 92.

As the photographing part 4 is moved forward, the endothelium reflection light En is moved rightward in the image (see FIG. 9B). When the endothelium reflection light En reaches the second detection region Lc2, the total value SLC2 increases (see an inclination B in FIG. 10B). While the endothelium reflection light En is being received on the second detection region Lc2, a high value is maintained. When the photographing part 4 is moved more forward and the endothelium reflection light En passes the detection region Lc2, the total value SLC2 greatly decreases (see FIG. 9C and an inclination C in FIG. 10B). When the total value decreases below a predetermined threshold S2, the controller 90 reduces the light intensity of the light source 12 (including turn-off of the light source 12) and also stops driving of the drive part 6 to stop the forward movement of the photographing part 4.

After termination of the serial photographing to the corneal central part as above, the controller 90 changes the fixation direction of the eye E and shifts serial photographing to a next photographing position. The controller 90 then turns on the light source 71d. Accordingly, the visual line of the eye E is guided upward and the photographing position is set to the lower part relative to the central part of the cornea.

The controller 90 turns on the light source 12 again with such a light intensity as to make an endothelial image appear in the image outputted from the imaging element 44. The controller 90 controls driving of the drive part 6 to move the photographing part 4 backward with respect to the eye E. It is preferable to start the backward movement after the visual line of the eye E is stabilized (for example, after a lapse of a predetermined time (e.g., after 1 second) from the change of the fixation direction).

After the light source 12 is turned on again, the controller 90 continues to move the photographing part 4 backward and causes the memory 92 to store, at any time, imaged images serially outputted from the imaging element 44. As the photographing part 4 is moved backward, the endothelium reflection light En is moved leftward in the image. In this case, the image changes from FIG. 9C to FIG. 9A in reverse order to the chances from FIG. 9A to FIG. 9C.

Thereafter, when the photographing part 4 is moved backward and the epithelium reflection image Ep reaches the first detection region Lc1, the total value SLC1 increases. When the total value SLC1 exceeds the predetermined threshold S1, the controller 90 reduces the light intensity of the light source 12 (including turn-off of the light source 12) and stops driving of the drive part 6 to stop the backward movement of the photographing part 4.

When serial photographing to the lower part of the cornea is terminated, successively, the controller 90 changes the fixation direction of the eye E and shifts to serial photographing to a next photographing position. The controller 90 then turns on the light source 71b. Accordingly, the visual direction of the eye E is guided to the right so that the photographing position is set to the left part relative to the corneal central part.

The controller 90 further turns on the light source 12 again with such a light intensity as to make an endothelial image appear in the image outputted from the imaging element 44. The controller 90 also controls driving of the drive part 6 to move the photographing part 4 forward with respect to the eye E. After the light source 12 is turned on again, the controller 90 continues to move the photographing part 4 backward and causes the memory 92 to store, at any time, imaged images serially outputted from the imaging element 44. Subsequent operations are similar to those in the photographing control with the light source 71a being lighted and the photographing control with the light source 71d being lighted, and thus the details are not explained.

Specifically, while turning on the light source 71b, the controller 90 moves the photographing part 4 forward and also keeps the light source 12 continuously turned on to perform serial photographing to the left part of the cornea. Thereafter, while turning on the light source 71h, the controller 90 moves the photographing part 4 backward and also keeps the light source 12 continuously turned on to perform serial photographing to the upper part of the cornea. The controller 90 further, while turning on the light source 71f, moves the photographing part 4 forward and also keeps the light source 12 continuously turned on to perform serial photographing to the right part of the cornea. When the endothelial image is obtained at each photographing position corresponding to the first photographing pattern, the controller 90 terminates the photographing operation and moves the photographing part 4 back to an initial position.

The controller 90 causes the memory 92 to store images outputted from the imaging element 44 in association with photographing points. This association includes the association with the light sources turned on at the time of obtaining each image. The controller 90 thereafter chooses from the images stored in the memory 92 by image processing and displays the endothelial image on the screen of the monitor 95.

As above, the first endothelial image is serially obtained while the photographing part 4 is moving forward and the second endothelial image at a different point from the first endothelial image is serially obtained while the photographing part 4 is moving backward (in a returning direction), so that the endothelial images at different positions can be smoothly obtained. In the case where the photographing points are three or more, the above operation is repeated, so that the endothelial images at three or more points can be smoothly obtained.

In this case, for example, the position of the fixation target is changed according to the change of the moving direction of the photographing part 4. Thus, the endothelial image at each position of the cornea can be smoothly obtained. Change of the moving direction and change of the fixation position are not necessarily performed at the same time.

When the fixation position is to be changed in the reciprocating movement, the controller 90 may determine whether or not the fixation state of the eye E is stabilized based on the photographing signal from the imaging element 84, and start the forward or backward movement based on the determination result. For instance, the controller 90 may start the forward or backward movement when the misalignment in the X-Y direction detected as above falls in a predetermined tolerance range.

The method of keeping the light source 12 turned on continuously includes a method of always turning on the light source 12 and also a method of continuously blinking the light source 12. In the case where the light source 12 is continuously blinked, for example, the controller 90 causes the light source 12 to blink to obtain a plurality of endothelial images during movement of the photographing part 4. Further, the light source 12 may be blinked continuously in sync with the frame rate of the two-dimensional imaging element 44. For instance, in the case where the photographing time for one image is 30 ms, the light source 12 is kept turned on for several milliseconds from the start to obtain the image and then the light source 12 is turned off, and further the light source 12 is turned on when a next image starts to be obtained. That is, such blinking operation is repeated.

Not limited to the above, the controller 90 has only to control the light source 12 to emit light several times (naturally including continuous light emission) so that a plurality of endothelial images are obtained by the imaging element 44.

As the timing of turning off the light source 12 (reducing the light intensity of the light source 12) when the photographing part 4 is moved backward, the controller 90 also may turn off the light source 12 and stop the photographing part 4 at the time when the epithelial peak reaches a predetermined position (e.g., a center position) on the one-dimensional light-receiving element 89 and, of course, not limited thereto. For instance, the controller 90 also may detect a moving distance of the photographing part 4 from the start of backward movement thereof and, when the distance reaches a predetermine value, turn off the light source 12 and stop the photographing part 4.

Further, the controller 90 has only to detect a light receiving state of the corneal reflection light (including epithelium reflection light and endothelium reflection light) on the imaging element 44 and, based on a detection result, perform at least either the control of the light intensity of the light source 12 or the stop of the backward movement. For instance, the controller 90 also may detect the light receiving state of the corneal reflection light based on the light reception signal from the one-dimensional light-receiving element 89.

For instance, the controller 90 causes the memory 92 to store a detection position of the epithelial peak when the endothelial peak reaches a predetermined position on the light-receiving element 89 (or the imaging element 44) in the photographing to the corneal central part. When moving the photographing part 4 backward, the controller 90 uses as a trigger that the epithelium reaches the detection position stored in the memory 92, and thus at least either turns off the light source 12 (reduces the light intensity of the light source 12) or stops the backward operation. In this case, it is preferable to turn off the light source 12 (reduce the light intensity of the light source 12) or stop the backward operation after the epithelium having reached the detection position moves by a predetermined distance.

In the above explanation, a returning position of the photographing part 4 for reciprocating movement is set based on the output images from the imaging element 44, but not limited thereto. Specifically, it may be arranged to detect the light receiving state of the corneal reflection light (including epithelium reflection light and endothelium reflection light) on the imaging element 44 and set the returning position based on the detection result. For instance, the controller 90 also may detect the light receiving state of the corneal reflection light based on the light reception signal from the one-dimensional light-receiving element 89. Accordingly, the moving distance, the turn-on time of the light source, and others can be shortened.

For controlling the light source 12 based on the output image from the imaging element 44, the controller 90 may monitor change amounts of the total values SLC1 and SLC2 for a predetermined time and turns on/off the light source 12 when the change amounts exceed a predetermined threshold value. In this case, the controller 90 may perform differential processing of the total values SLC1 and SLC2 per unit time.

The above explanation exemplifies the case where the photographing part 4 is reciprocally moved back and forth, but is not limited thereto. For instance, the controller 90 reciprocally moves the photographing part 4 in a direction perpendicular to the optical axis L1 of the anterior segment observation optical system 80 (e.g., up-and-down and right-and-left directions) to perform serial photographing respectively in the forward direction and the backward direction. The controller 90 further may move the photographing part 4 in the up-and-down and right-and-left directions while reciprocally moving in the back-and-forth direction.

<Continuous Photographing in X-Y Direction>

The controller 90 generally moves the photographing part 4 in the X-Y direction by controlling driving of the drive part 6 and serially photographs cell images at different positions on the cornea in the X-Y direction. For instance, the controller 90 moves the photographing part 4 linearly in the X-Y direction to serially obtain the endothelial images.

Figure 11A:
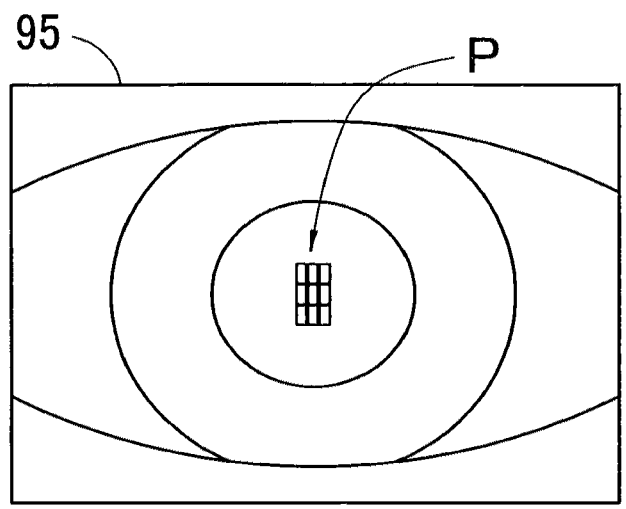
FIG. 11A is a diagraph showing one example of a photographing range set on a cornea.
Figure 11B:
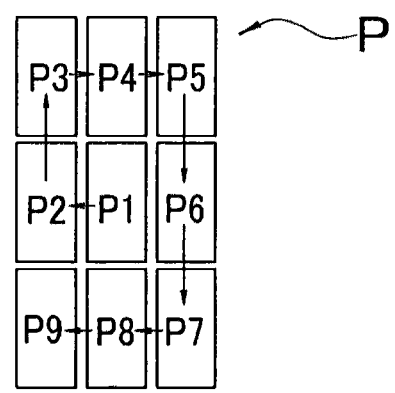
FIG. 11B is an enlarged view of the photographing range shown in FIG. 11A.

FIG. 11A is a diagram showing one example of a photographing range set on the cornea. FIG. 11B is an enlarged view showing the photographing range shown in FIG. 11A. A photographing range P includes a plurality of photographing points present in at least any of up-down, right-left, and oblique positions around a corneal center P1. In this case, for example, an alignment position obtained when the corneal center coincides with the observation optical axis L1 is set as a reference position and a moving amount of the photographing part 4 to each photographing position corresponding to each photographing point is set.

In FIGS. 11A and 11B, the photographing range P corresponds to nine points including photographing points P1 to P9. The photographing range P may be a range in which photographing points are arranged in one line along a certain straight direction (e.g., a right and left direction) or a range in which photographing points are arranged in a circle. The photographing range P may be a previously set range or a range set by an examiner (the details will be mentioned later). As another alternative, it may be possible to prepare two or more kinds of photographing ranges in advance and allow an examiner to select a certain one of the photographing ranges.

Subsequently, the controller 90 controls driving of the drive part 6 to move the photographing part 4 toward a position corresponding to each photographing point. The photographing order to each photographing point is set in advance. For instance, the controller 90 moves the photographing part 4 so that the photographing part 4 draws a predetermined path (see arrows in the enlarged view) from the photographing point P1 as a start, followed by the subsequent photographing points P2, P3, . . . in order. The controller 90 causes the illumination light source 12 to emit light for each photographing position and obtains the endothelial cell images in series through the imaging element 44. The thus obtained cell images are stored in association with the photographing points P1 to P9 in the memory 92.

The controller 90 may continuously move the photographing part 4 in the photographing range P and cause the illumination light source 12 to continually emit light (including always turning-on and flashing at predetermined time intervals) during movement of the photographing part 4 to serially photograph the cell images. The controller 90 further may photograph the cell images while stopping the photographing part 4 at each photographing position.

Figure 12:
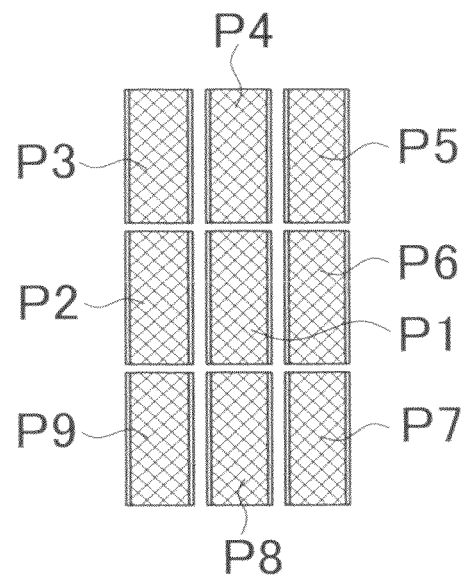
FIG. 12 is a diagram showing one example when each cell image is displayed in a display format conforming to a positional relationship between photographing points on a screen of a monitor.

After the serial photographing is completed as above, the controller 90 causes the monitor 95 to display each cell image on the screen in the display format matching with the positional relationship between the photographing points as shown in FIG. 12. The display format is not limited thereto and may include parallel display to display the cell images arranged in a predetermined number of parallel rows (e.g., two rows). The controller 90 also may display a predetermined number of images (e.g., three images) on the monitor 95 and update the image by operation of the examiner.

With the above configuration, the cell images related to a plurality of positions near the corneal center can be smoothly obtained without changing the visual direction of the eye E. For instance, a cell image can be obtained in a wider photographing range as compared with the endothelium photographing to a fixed position.

The above explanation provides the configuration to serially photograph different points in the X-Y direction while the fixation position is fixed at the center, but is not limited thereto. Specifically, it is only necessary to serially obtain a plurality of cell images by changing the X-Y position of the photographing part 4 with respect to the eye E while the fixation direction of the eye E is fixed in a certain direction. For instance, while the fixation position is fixed to an upper part, serial photographing is performed to different points in the X-Y direction. Accordingly, the cell image in a lower area of the peripheral part of the cornea is obtained in a wide photographing range.

In the above X-Y serial photographing, the controller 90 also may serially photograph endothelial cells at different positions in the back-and-forth direction at each photographing position. For instance, the controller 90 moves the photographing part 4 in the back-and-forth direction at each photographing position and causes the illumination light source 12 to continuously emit light during the back and forth movement to obtain a plurality of cell images at each position.

In this case, the controller 90 may perform the serial photographing by moving the photographing part 4 in the Z direction while stopping the movement of the photographing part 4 in the X-Y direction. The controller 90 may also perform the serial photographing by moving the photographing part 4 in the Z direction during movement thereof in the X-Y direction.

<Z-Alignment Determination and Positional Adjustment to Each Photographing Position>

In the above X-Y serial photographing, when the position in the X-Y direction is changed, alignment in the Z direction may be displaced. For example, the cornea has a curved surface and thus the endothelial position in the Z direction differs from a photographing point to another. The controller 90 therefore may perform automatic alignment in the Z direction during operations during the X-Y serial photographing.

For instance, the controller 90 analyzes by image processing the imaged image obtained by the imaging element 44 and then determines whether or not the obtained imaged image includes the endothelial cell image. By use of the determination result, the controller 90 moves the photographing part 4 in the back-and-forth direction so that the endothelial cell image is included in the imaged image. In this case, the presence/absence of the endothelial cell image may be determined by using the luminescent level and the area of the endothelial cell image or it may be determined whether or not the position of the endothelial cell image on the imaging element 44 is in a predetermined position.

FIG. 13 are diagrams showing one example to detect alignment in the Z direction using the endothelial cell image imaged by the imaging element. When the first endothelial image corresponding to the photographing point P1 is to be obtained, the controller 90 controls driving of the drive part 6 to activate the automatic alignment with respect to the photographing point P1. After completion of the XYZ alignment, the controller 90 moves the photographing part 4 forward and serially photographs the endothelial image.

Figure 13A:
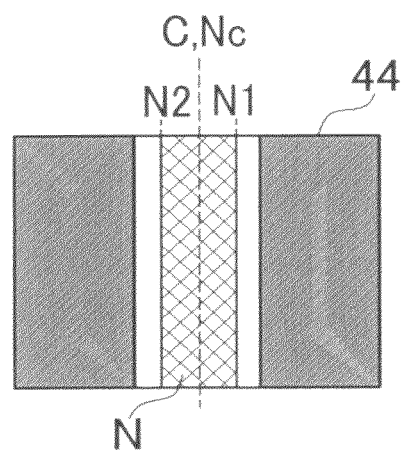
FIGS. 13A and 13B are diagrams showing one example to detect alignment in a Z direction using a cell image imaged by the imaging element.
Figure 13B:
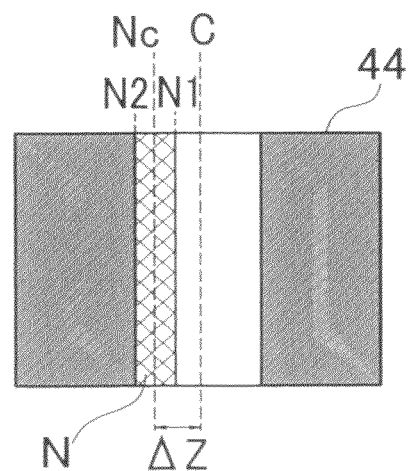

Herein, the controller 90 continuously turns on the illumination light source 12 and controls driving of the drive part 6 so that the endothelial cell image is included in the photographed image obtained by the imaging element 44. For instance, the controller 90 detects a first edge N1 and a second edge N2 based on luminescence distribution of the endothelial image N (for example, edge detection) as shown in FIGS. 13A and 13B and detects an intermediate position Nc of the first edge N1 and the second edge N2. The controller 90 can discriminate the epithelial image and the endothelial image based on the luminescence, the order of appearance, and others.

When the center position Nc of the endothelial image N is detected, the controller 90 controls driving of the drive part 6 so that the center position Nc is formed at a predetermined position C on the imaging element 44. When an image including an endothelial image N comes to the center of the imaging element 44, the controller 90 determines that photographing to the photographing point P1 is completed.

The controller 90 then moves the photographing part 4 in the X-Y direction and further moves the photographing part 4 to the photographing points P2 to P9 in turn. Herein, in addition to the movement of the photographing part 4 in the X-Y direction, the controller 90 detects a displacement AZ of the center position Nc from the predetermined position C on the imaging element 44 and then moves the photographing part 4 so that the displacement AZ falls in a tolerance range. If the displacement AZ is in the tolerance range, the controller 90 stops driving of the drive part 6 in the Z direction. If the displacement AZ is out of the tolerance range, on the other hand, the controller 90 controls driving of the drive part 6 in the Z direction. Thus, the photographing part 4 is moved in the direction to cancel the displacement.

As above, even when the photographing position in the X-Y direction is changed, the alignment position in the Z direction is adjusted. The cell image at each photographing position can be stably obtained.

The controller 90 may obtain the Z-direction alignment positional information Za based on the light reception result of the light-receiving element 89 when the endothelial image is obtained at a first position (another photographing position is available) corresponding to the first photographing point P1, and then control driving of the drive part 6 so that the photographing part 4 is moved to the alignment position corresponding to the positional information Za.

The controller 90 causes the memory 92 to store the light reception result of the light-receiving element 89 when the endothelial image is obtained at the first position. In the serial photographing in the X-Y direction, the controller 90 detects the alignment state in the Z direction based on the light reception signal outputted from the light-receiving element 89. The controller 90 performs feedback control of the drive part 6 so that the light reception result of the light-receiving element 89 becomes the positional information Za.

For instance, the controller 90 causes the memory 92 to store the position of the epithelium when the endothelial image is obtained, and performs feedback control of the drive part 6 so that the epithelial image is received at the position stored in the memory 92.

The controller 90 may detect the light reception signal corresponding to the endothelium reflection in the alignment detection using the light-receiving element 89. In the serial photographing in the X-Y direction, for example, the controller 90 performs the feedback control of the drive part 6 so that a peak of the light reception signal by the reflection light from the endothelium comes to a predetermined position (e.g., a center position) on the light-receiving element 89.

<XY-Alignment Determination to Each Photographing Position>

The above apparatus may be configured to detect a relative position of the photographing part 4 with respect to the eye E and then perform alignment guidance and alignment determination to each photographing position based on the detection result.

The controller 90 generally moves the photographing part 4 based on the detection result of the XY alignment and adjusts the photographing position to the vicinity of the corneal center. After adjusting the photographing position to the vicinity of the corneal center, the controller 90 moves the photographing part 4 in the up-and-down and right-and-left directions to obtain the endothelial images near the corneal center in series through the imaging element 44. In this case, for example, if it is in a range where the examinee's eye can visually recognize the fixation lamp for photographing the corneal central part, it is possible to adjust the photographing position.

For example, the controller 90 activates the automatic alignment with respect to each photographing position, thereby sequentially automatically moving the photographing part 4 to each photographing position. The endothelial cell image at each photographing position is obtained. At that time, the controller 90 changes the alignment completion position of the photographing part 4 with respect to the eye E according to the change of the photographing position.

Figure 14:
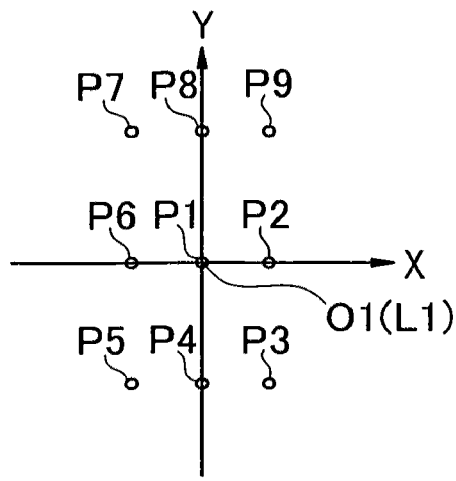
FIG. 14 is a diagram showing a light receiving position of an index image corresponding to each photographing position.

FIG. 14 shows a light receiving position of the index HO corresponding to each photographing position. For instance, the alignment completion position on the imaging element 84 in relation to each photographing position P1 to P9 is stored in the memory 92 in advance. At that time, the position at which the corneal center and the optical axis L1 coincide with each other is used as a reference position O1. In other words, in relation to the photographing positions P1 to P9, a distance between a light reception position K1 while the optical axis L1 is aligned with the photographing position and the reference position O1 is set as an offset amount.

Figure 15A:
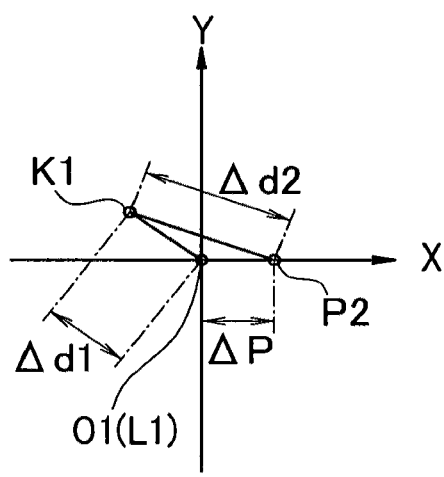
FIGS. 15A and 15B are diagrams showing one example of an alignment detecting method when an endothelial cell image of a certain photographing point.
Figure 15B:
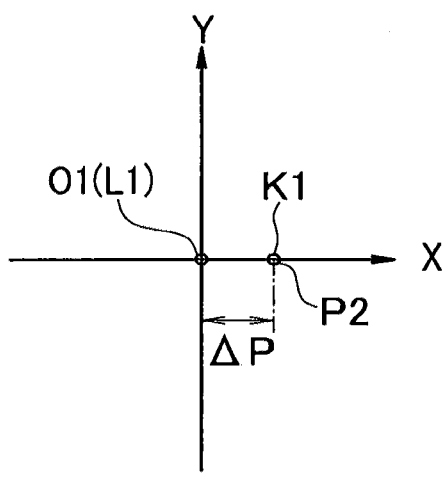

FIGS. 15A and 15B are diagrams showing one example of an alignment detecting method to obtain an endothelial cell image at a certain photographing point (P2). To obtain the endothelial image corresponding to the photographing point P1, the controller 90 detects an alignment deviation amount Δd1 between the reference position O1 and the light receiving position K1. The controller 90 drives the drive part 6 so that the deviation amount Δd1 falls in the tolerance range and then captures the endothelial image.

After termination of the photographing to the photographing point P1, the controller 90 subtracts an offset amount ΔP from the alignment deviation amount Δd1 defined between the reference position O1 and the light receiving position K1. The controller 90 further detects an alignment deviation amount Δd2 obtained by multiplying the deviation amount Δd1 by the offset amount ΔP.

The controller 90 drives the drive part 6 so that the deviation amount Δd2 falls in a tolerance range and then images the endothelial image. Thereafter, the controller 90 changes the photographing position and performs automatic alignment and photographing with respect to the changed photographing position.

When the serial photographing in the X-Y direction is to be performed, accordingly, respective cell images for the set photographing positions can be stably obtained.

The above explanation provides the configuration to detect the alignment state with respect to the eye E by detecting a corneal luminescent spot, but is not limited thereto. The alignment state may be detected by detecting a characteristic portion of the eye E by the image processing. For instance, the alignment is detected by detecting the pupil center of the eye E. At that time, the position at which the pupil center and the optical axis L1 coincide with each other may be used as the reference photographing position.

<Change of Photographing Area by Examiner>

Figure 16:
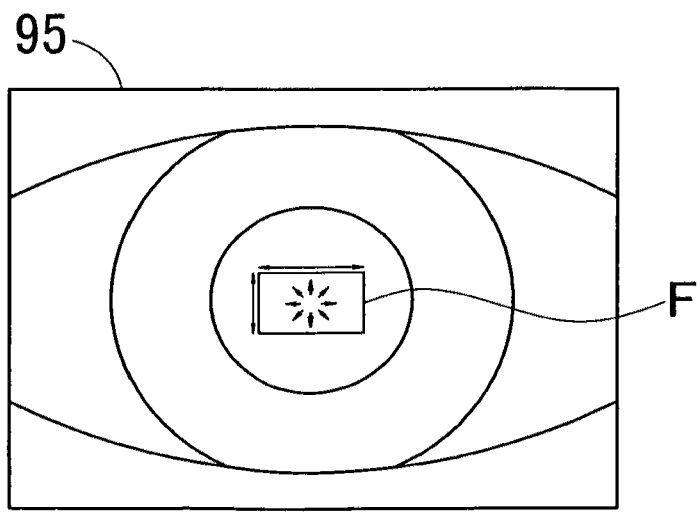
FIG. 16 is a diagram showing one example when the photographing range is set on a monitor.

FIG. 16 is a diagram showing one example to set a photographing range P on the monitor 95. When the photographing range is to be set on the anterior segment displayed on the monitor 95, the controller 90 may electronically display a frame F corresponding to the photographing range on the monitor 95. The controller 90 changes the position and the size of the frame F displayed on the screen of the monitor 95 based on the operation signal input by a predetermined operating member set to change the photographing range.

As the operating member to set the photographing range, for example, a predetermined switch provided on the operation part 96 is used. Further, it may be a touch panel formed on the screen of the monitor 95.

The controller 90 changes the photographing range according to the change of the frame F based on the operating member. In this case, a corresponding relationship between the display position of the frame F on the monitor 95 and the relative position of the photographing part 4 with respect to the eye E is stored in advance in the memory 92. Regarding the photographing position in the X-Y direction within the photographing range, each photographing position may be set at predetermined intervals or each photographing position may be set arbitrarily.

After the frame F is adjusted, when the photographing switch 5b is pressed, the controller 90 moves the photographing part 4 in sequence so that the endothelial image in the set photographing range is photographed, and obtains the cell image at each photographing position.

In the case of performing serial photographing as above, the internal fixation optical systems 70a to 70i are preferably configured to project infinite light to the eye E. With the above configuration, even when the photographing part 4 is moved in the X-Y direction with respect to the eye E, the visual line direction of the eye E is maintained and thus cell images at different X-Y positions are stably obtained.

The present invention is not limited to the aforementioned embodiment and may be embodied in other specific forms without departing from the essential characteristics thereof.

The invention claimed is:

1. A corneal endothelial cell photographing apparatus comprising:
   a main unit including:
      an illumination optical system for illuminating illumination light from an illumination light source toward a cornea of an examinee's eye from an oblique direction;
      an imaging optical system for obtaining a corneal endothelial cell image by receiving, through an imaging element, reflection light from the cornea including corneal endothelial cells; and
      a fixation optical system including a plurality of fixation targets and for guiding a fixation direction of the examinee's eye;
   a drive unit operable to relatively move the main unit with respect to the examinee's eye in a three-dimensional rectangular coordinate system having a first axis in a back-and-forth direction toward and away from the examinee's eye, a second axis in an up-and-down direction relative to the examinee's eye, and a third axis in a right-and-left direction relative to the examinee's eye;
   a controller configured to operate the main unit in correlation with the drive unit and the fixation optical system to obtain endothelial photographic images in series at a plurality of photographing points of a preset photographing pattern on the cornea by way of relative movement between the main unit and the cornea in at least one of the up-and-down direction and the right-and-left direction, wherein the photographing points of the preset photographing pattern are different on the cornea from one another in at least one of the up-and-down direction and the right-and-left direction; and a display control unit for causing a monitor to display the obtained endothelial image.

2. The corneal endothelial cell photographing apparatus according to claim 1, wherein the controller previously sets a fixation target group to be presented to the examinee from the fixation targets and an order of the fixation of the targets in the fixation target group to be presented, the controller is configured to control the fixation optical system to present a fixation target at a first fixation position based on the order of the fixation targets to be presented previously set in the fixation target group and control the illumination optical system and an imaging optical system to obtain an endothelial image of a first point of the cornea, the controller is configured to cause the monitor to display the endothelial image obtained of the first point of the cornea; and after the endothelial image of the first point of the cornea is obtained, the controller is configured to control the fixation optical system to change a presenting position of the fixation target to a second fixation position based on the order of the fixation targets to be presented previously set in the fixation target group, thereby causing relative movement between the main unit and the cornea in at least one of the up-and-down direction and the right-and-left direction, and control the illumination optical system and the imaging optical system to obtain an endothelial image of a second point of the cornea.

3. The corneal endothelial cell photographing apparatus according to claim 2, further including an operating part to be operated by an examiner to previously set the fixation target group to be presented to the examinee from the fixation targets.

4. The corneal endothelial cell photographing apparatus according to claim 2, further including an anterior segment observation optical system having an anterior segment imaging element to image an anterior segment of the examinee's eye, wherein the controller determines whether or not a fixation state of the examinee's eye has stabilized based on an imaging signal from the anterior segment imaging element and then starts an operation to obtain the endothelial image based on a determination result.

5. The corneal endothelial cell photographing apparatus according to claim 1, wherein the controller controls driving of the drive unit to shuttle the main unit in a predetermined direction and causes the illumination light source to emit light two or more times during movement of the main unit in a forward direction to obtain a plurality of endothelial images in a first photographing point through the imaging element, while causing the illumination light source to emit light two or more times during movement of the main unit in a backward direction to obtain a plurality of endothelial images in a second photographing point through the imaging element.

6. The corneal endothelial cell photographing apparatus according to claim 5, wherein the controller detects a light reception state of corneal reflection light on the imaging element and sets a returning position based on a detection result.

7. The corneal endothelial cell photographing apparatus according to claim 1, wherein the controller previously sets a photographing range on the cornea including the pattern of the photographing points that are different from one another in at least one of the up-and-down direction and the right-and-left direction, and the controller is configured to operate the drive unit to move the main unit in the up-and-down direction and the right-and-left direction and to operate the main unit to serially obtain endothelial images at the plurality of photographing points in the previously set photographing range.

8. The corneal endothelial cell photographing apparatus according to claim 7, further including a Z alignment detection sensor for detecting an alignment state in the back-and-forth direction with respect to the cornea at each photographing point, and wherein the controller is configured to control the drive unit based on a detection result of the Z alignment detection sensor to adjust a back-and-forth position of the main unit at each photographing point.

9. The corneal endothelial cell photographing apparatus according to claim 7, further including a setting unit to be operated by an examiner to set the photographing range on a corneal image displayed on the monitor.

10. The corneal endothelial cell photographing apparatus according to claim 7, wherein the controller moves the main unit in the back-and-forth direction at each photographing point, and serially obtains endothelial images at different photographing positions in the back-and-forth direction through the imaging element.

11. The corneal endothelial cell photographing apparatus according to claim 1, further including an XY alignment detection sensor for detecting an alignment state in the up-and-down direction and the right-and-left direction with respect to a corneal center of the examinee's eye, wherein the controller controls driving of the drive unit based on a detection result of the XY alignment detection sensor to move the main unit to the photographing points while obtaining endothelial images at the photographing points.

12. The corneal endothelial cell photographing apparatus according to claim 1, wherein the controller is configured to sequentially change the photographing points clockwise or counterclockwise.

13. The corneal endothelial cell photographing apparatus according to claim 1, wherein, when serial photographing in the up-and-down direction and the right-and-left direction is to be performed, the controller is configured to detect a relative position of the main unit with respect to the eye at each of the photographing points and perform automatic alignment to each of the photographing points.

14. The corneal endothelial cell photographing apparatus according to claim 13, wherein the controller is configured to perform automatic alignment in the back-and-forth direction to each of the photographing points.

15. The corneal endothelial cell photographing apparatus according to claim 14, wherein the controller is configured to perform automatic alignment in at least one of the up-and-down direction and the right-and-left direction to each of the photographing points.

* * * * *